United States Patent
Huang et al.

(10) Patent No.: US 10,258,556 B2
(45) Date of Patent: Apr. 16, 2019

(54) ANTI-AGING PEPTIDE, ITS COMPOSITION AND METHOD OF USING THE SAME

(71) Applicant: Yu-Chun Liu, Taoyuan (TW)

(72) Inventors: Min-Chuan Huang, Taipei (TW); Syue-Ting Chen, Taipei (TW); Yu-Chun Liu, Taoyuan (TW)

(73) Assignee: Yu-Chun Liu, Taoyuan (TW)

( * ) Notice: Subject to any disclaimer, the term of this patent is extended or adjusted under 35 U.S.C. 154(b) by 0 days.

(21) Appl. No.: 15/626,775

(22) Filed: Jun. 19, 2017

(65) Prior Publication Data

US 2018/0360720 A1    Dec. 20, 2018

(51) Int. Cl.

| | |
|---|---|
| *A61K 8/38* | (2006.01) |
| *A61K 8/64* | (2006.01) |
| *C07K 7/06* | (2006.01) |
| *A61Q 19/08* | (2006.01) |
| *A61K 8/04* | (2006.01) |
| *A61K 8/02* | (2006.01) |
| *A61Q 19/02* | (2006.01) |
| *A61K 38/08* | (2019.01) |

(52) U.S. Cl.
CPC .............. *A61K 8/64* (2013.01); *A61K 8/0212* (2013.01); *A61K 8/04* (2013.01); *A61K 38/08* (2013.01); *A61Q 19/02* (2013.01); *A61Q 19/08* (2013.01); *C07K 7/06* (2013.01)

(58) Field of Classification Search
None
See application file for complete search history.

(56) References Cited

PUBLICATIONS

NCBI Blast output for SEQ ID 1, program run Nov. 13, 2018.*
GenBank entry BAA92597, entered Jul. 26, 2016.*

\* cited by examiner

*Primary Examiner* — Fred H Reynolds
(74) *Attorney, Agent, or Firm* — Birch, Stewart, Kolasch & Birch, LLP

(57) ABSTRACT

Disclosed is related to an anti-aging peptide, which has an amino acid sequence of ProAspSerThrGluAlaLys (SEQ ID NO: 1). Also provided are anti-aging compositions comprising the peptide and personal care methods of using the peptide.

11 Claims, 3 Drawing Sheets

Specification includes a Sequence Listing.

SEQUENCE LISTING

```
<160> NUMBER OF SEQ ID NOS: 11

<210> SEQ ID NO 1
<211> LENGTH: 7
<212> TYPE: PRT
<213> ORGANISM: Artificial Sequence
<220> FEATURE:
<223> OTHER INFORMATION: Synthetic

<400> SEQUENCE: 1

Pro Asp Ser Thr Glu Ala Lys
1               5
```

```
<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
gaacatccgg agcccagagg                                               20

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
tccatgttgc agaagacttt                                               20

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
ggtgaagatg gtcaccctgg                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
ggggcaccag gttcaccctt                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
cgccctccta atggtcaagg                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
ttctgaggac cagtagggca                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 8
ccttccccgc agttaccttt                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
tgcagacact cctaagccac                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
cgtgcgtgac attaaggaga                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
gaaggaaggc tggaagagtg                                              20
```

ANTI-AGING PEPTIDE, ITS COMPOSITION AND METHOD OF USING THE SAME

REFERENCE TO SEQUENCE LISTING SUBMITTED VIA EFS-WEB

This application includes an electronically submitted sequence listing in .txt format. The .txt file contains a sequence listing entitled "2017-09-07-SEQ-LISTING-5992-0165PUS1-ST25.txt" created on Sep. 7, 2017 and is 2,239 bytes in size. The sequence listing contained in this .txt file is part of the specification and is hereby incorporated by reference herein in its entirety.

FIELD OF THE INVENTION

The present invention relates generally to an anti-aging peptide, the method of using it and the composition thereof.

BACKGROUND OF THE INVENTION

Typical skin damage includes thinning of the skin, occurring naturally as one ages. There is a reduction in the cells and blood vessels that supply the skin as well as a decrease in thickness of the dermis. Damages or changes in aging or damaged skin include wrinkling, fine lines, hyperpigmentation, sallowness, dark undereye circles, puffy eyes, diminished rate of turnover, and abnormal desquamation or exfoliation. Some other damages include visible dead skin, such as flaking, scaling, dryness, roughness. With skin aging, total collagen content in the dermis decreases and the remaining collagen fibers become thicker gradually, leading to increased crosslinking and decreased solubility, extensibility, etc. In addition, elastin becomes thicker and more crosslinked. Besides, proliferative activity of fibroblasts in the dermis decreases whereas collagen synthesizing ability decreases and degrading ability increases. As the regeneration of the epidermis, dermis, etc. becomes slow and the adhesion between the epidermis and the dermis becomes weak, the skin elasticity is decreased rapidly.

Although some products have been developed to improve the condition of aged skin, there is still a need for compositions and methods for remedy for damages, such as skin damages, caused by aging or changes in aged skin.

BRIEF SUMMARY OF THE INVENTION

It is unexpectedly found in the present invention that a peptide having the amino acid sequence of ProAspSerThrGluAlaLys (SEQ ID NO: 1) is effective in the enhancement of collagen and/or elastin levels, and the migration of the fibroblast cells in a subject.

Accordingly, the present invention provides in one aspect an anti-aging peptide, which is a synthetic peptide consisting of the amino acid sequence of SEQ ID NO: 1. The peptide provides an effect in enhancing the expression of collagen or elastin in fibroblast cells, and the migration of fibroblast cells.

In another aspect, the present invention provides a personal care composition. The composition comprises an effective amount of the peptide of SEQ ID NO: 1.

In certain embodiments of the invention, the composition may further comprise an acceptable carrier, and may be formulated as a topical formulation, such as a cosmetic formulation.

According to the present invention, the topical formulation may comprise an ointment, lotion, cream, gel, drops, spray, liquid, or face mask. In one preferred embodiment, the composition is formulated as a cream or a face mask.

In one further aspect, the present invention provides a personal care method for remedy for damages caused by aging, which comprises administering to a subject in need thereof the peptide having the amino acid sequence of SEQ ID NO: 1 in an amount effective to enhance the expression of collagen or elastin, or the migration of the fibroblast cells in the subject.

In one embodiment of the method according to the invention, the peptide is topically administered to the subject.

In one example of the invention, the method is particularly used for skin care.

According to the invention, the method is used to provide anti-ageing, brightening-skin efficacy and an efficacy.

It is to be understood that both the foregoing general description and the following description are exemplary and explanatory only and are not restrictive of the invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred.

In the drawings.

DETAILED DESCRIPTION OF THE INVENTION

Figure 1:
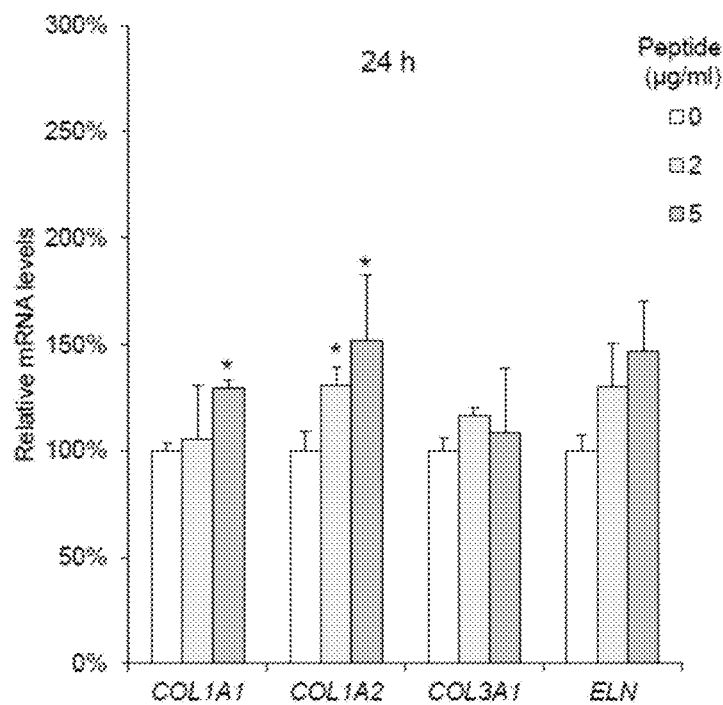
FIG. 1 shows the effect of the peptide of SEQ ID NO: 1 in increasing the expression of collagen and elastin in CCD-966SK fibroblast cells; wherein the mRNA levels of collagen (COL1A1, COL1A2 and COL3A1) and elastin (ELN) in CCD-966SK fibroblast cells treated with the peptide of SEQ ID NO: 1 at different concentrations for 24 hours (upper panel) or 48 hours (lower panel) were analyzed by real-time RT-PCR ($*P<0.05$; $**P<0.01$).
Figure 1:
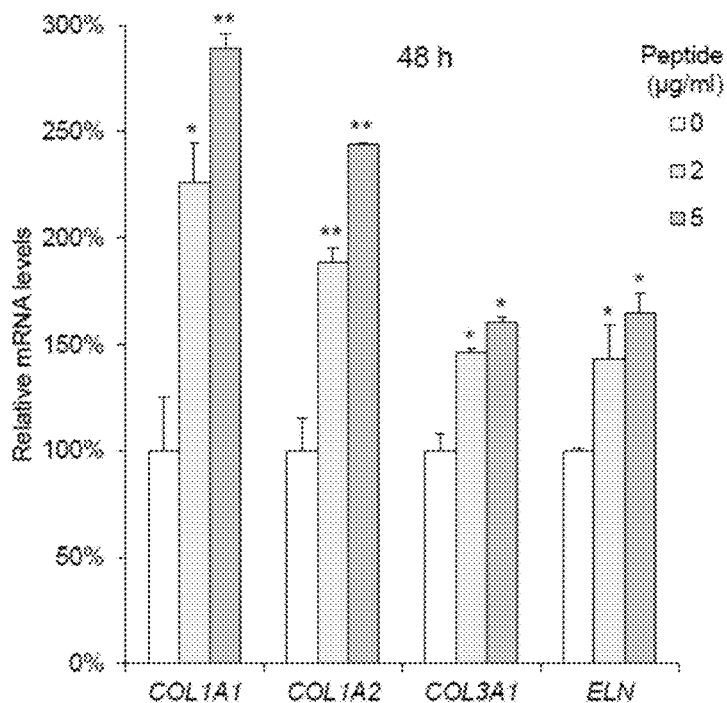

Unless defined otherwise, all technical and scientific terms used herein have the same meaning as commonly understood by those of ordinary skill in the art to which this invention belongs.

The use of the word "a" or "an" when used in conjunction with the term "comprising" in the claims and/or the specification may mean "one," but it is also consistent with the meaning of "one or more," "at least one," and "one or more than one."

The term "peptide" is used herein in its conventional sense, i.e., a polymer in which the monomers are amino acids and are joined together through amide bonds, alternatively referred to as a polypeptide. When the amino acids are α-amino acids, either the L-optical isomer or the D-optical isomer may be used. Additionally, unnatural amino acids, for example, β-alanine, phenylglycine and homoarginine are also meant to be included. Standard abbreviations for amino acids are used.

As used herein, the term "subject" refers to a vertebrate, preferably a mammal, particularly preferably a human. Hereinafter, a human serving as a subject is specifically referred to as a "human subject."

As used herein, the term "carrier" refers to materials commonly used on the formulation of pharmaceutical or cosmetic composition used to enhance stability, sterility and deliverability. When the peptide delivery system is formulated as a solution or suspension, the delivery system is in an acceptable carrier, preferably an aqueous carrier. A variety of aqueous carriers may be used, e.g., water, buffered water, 0.8% saline, 0.3% glycine, hyaluronic acid and the like. The compositions may contain physiologically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The term "topical" or "topically" is used herein its conventional sense as referring to a spot which can be in or on any part of the body, including but not limited to the epidermis, any other dermis, or any other body tissue. Topical administration or application means the direct contact of the peptide with tissue, such as skin or membrane which contains melanin-producing cells.

According to the present invention, the anti-aging peptide is a synthetic peptide consisting of the amino acid sequence of SEQ ID NO: 1, i.e., a sequence of ProAspSerThrGluAlaLys. The peptide may be artificially synthesized by a standard method or in any manner commonly used or known to one of ordinary skill.

As shown in the examples, the peptide having the amino acid sequence of SEQ ID NO: 1 was confirmed to have an effect in enhancing the expression of collagen or elastin, and the migration of the fibroblast cells. Therefore, the invention also provides a personal care method, which comprises administering to a subject in need thereof the peptide having the amino acid sequence of SEQ ID NO: 1 in an amount effective to enhance the expression of collagen or elastin in fibroblast cells, and the migration of the fibroblast cells.

On the other hand, the present invention provides an anti-aging composition. The composition comprises an effective amount of the peptide having the amino acid sequence of SEQ ID NO: 1. The composition provides an anti-aging efficacy, for example in skin, through the enhancement of the collagen or/and elastin levels, and the migration of the fibroblast cells in the subject. The composition may be used for cosmetic purposes, for example, skincare.

The present invention contemplates the use of the peptide of SEQ ID NO: 1 as an active ingredient for various uses. In one preferred embodiment, the peptide of the present invention is combined with an acceptable carrier to form a topical formulation which may be placed on the skin. Topical formulations, such as cosmetic formulations, may comprise an ointment, lotion, paste, cream, gel, drop, suppository, spray, liquid, powder and transdermal patch. Thickeners, diluents, emulsifiers, dispersing aids or binders may be used as needed. Preferably, one function of the carrier is to enhance skin penetration of the peptide of the present invention, and should be capable of delivering the peptide to fibroblasts under in vivo conditions. Suitable carriers are well known to one of ordinary skill, and include but are not limited to water, dimethylsulfoxide, ethanol, liposome, liquid petrolatum, petrolatum dimethylformamide, 2-pyrrolidone, oleic acid and etc.

Furthermore, the invention provides a personal care method for remedy for damages caused by ages. The method comprises administering to a subject in need thereof the peptide having the amino acid sequence of SEQ ID NO: 1 in an amount effective to enhance the expression of collagen or elastin in the fibroblast cells, or to enhance the migration of fibroblast cells in the subject. According to the invention, the method is used for anti-aging, brightening skin, reducing of wrinkling and fine lines in skin of said subject, particularly a human subject.

The present invention is further illustrated by the following examples, which are provided for the purpose of demonstration rather than limitation.

EXAMPLES

Example 1: Preparation of the Peptide of SEQ ID NO: 1

The peptide of SEQ ID NO: 1 (sequence: ProAspSerThrGluAlaLys) was synthesized by MDBio, Inc. (Taipei, Taiwan) and the purity and composition of peptide was confirmed by high performance liquid chromatography (HPLC) and mass spectrometry. Peptide stock was stored at −20° C. after dissolving 10 mg of lyophilized peptide powder in 250 μl of double deionized water ($ddH_2O$).

Example 2: Cell Cultures

CCD-966SK was skin fibroblast cells isolated from human breast and was purchased from BCRC (Bioresource Collection and Research Center, Hsinchu, Taiwan). It was cultured in Dulbecco's Modified Eagle Medium (DMEM) containing 10% (v/v) FBS and penicillin/streptomycin (100 IU/50 g/ml) in 5% $CO_2$ at 37° C.

Example 3: cDNA Synthesis and Quantitative Real-Time PCR

Total RNA was isolated using TRIzol reagent (Invitrogen) according to the manufacturer's protocol. For cDNA synthesis, 2 μg of total RNA was used in a 20 μl reverse transcription reaction using the High-Capacity cDNA Reverse Transcription Kits (AB, USA). QuantStudio 3 Real-Time PCR System (Thermo Fisher) was used for real-time PCR reactions. Reactions were performed in a 20-μl volume with 1 μl cDNA and 10 μl SensiFAST SYBR Lo-ROX Mix (BIOLINE). The cDNA was subjected to real-time PCR.

The following primer pairs were used:

```
(1) COL1A1
sense,
                                    (SEQ ID NO: 2)
5'-GAACATCCGGAGCCCAGAGG-3'
```

-continued and anti-sense, (SEQ ID NO: 3)
5'-TCCATGTTGCAGAAGACTTT-3';

(2) COL1A2
sense (SEQ ID NO: 4)
5'-GGTGAAGATGGTCACCCTGG-3'
and anti-sense, (SEQ ID NO: 5)
5'-GGGGCACCAGGTTCACCCTT-3';

(3) COL3A1
sense, (SEQ ID NO: 6)
5'-CGCCCTCCTAATGGTCAAGG-3'
and anti-sense, (SEQ ID NO: 7)
5'-TTCTGAGGACCAGTAGGGCA-3';

(4) ELN
sense, (SEQ ID NO: 8)
5'-CCTTCCCCGCAGTTACCTTT-3'
and anti-sense, (SEQ ID NO: 9)
5'-TGCAGACACTCCTAAGCCAC-3';

(5) β-actin
sense, (SEQ ID NO: 10)
5'-CGTGCGTGACATTAAGGAGA-3'
and anti-sense, (SEQ ID NO: 11)
5'-GAAGGAAGGCTGGAAGAGTG-3'.

The CCD-966SK fibroblast cells treated with the peptide of SEQ ID NO: 1 at different concentrations (0, 2 5 ug/ml) for 24 hours or 48 hours. The mRNA levels of collagen (COL1A1, COL1A2 and COL3A1) and elastin (ELN) of the cells were analyzed by real-time RT-PCR. As shown in FIG. 1, it was indicated that the peptide of SEQ ID NO: 1 increased the expression of collagen and elastin in the CCD-966SK fibroblast cells.

Example 4: Transwell Migration Assay

The cells ($5 \times 10^3$) in 0.25 ml serum-free DMEM were seeded into the upper chamber with an 8-μm pore size membrane (Corning, USA). Serum-free DMEM (0.5 ml) with or without MUC20 peptide NO.10 was loaded into the lower chamber in a well of 24-well culture plate. After 24 hours or 48 hours incubation, cells were fixed and stained with 0.5% (w/v) crystal violet (Sigma) containing 20% (v/v) methanol. The number of migrated cells from 5 random fields was counted under a phase-contrast microscope. Results were analyzed by student's t-test and graphed as mean±SD. The results were obtained from two independent experiments.

Figure 2A:
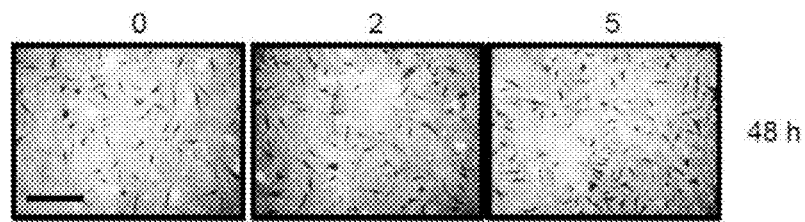
FIG. 2A shows the representative images of the migrated cells for 48 hours; wherein the migration of the CCD-966SK fibroblast cells treated with the peptide of SEQ ID NO: 1 at different concentrations was analyzed by transwell migration assay (scale bar=100 μm).
Figure 2B:
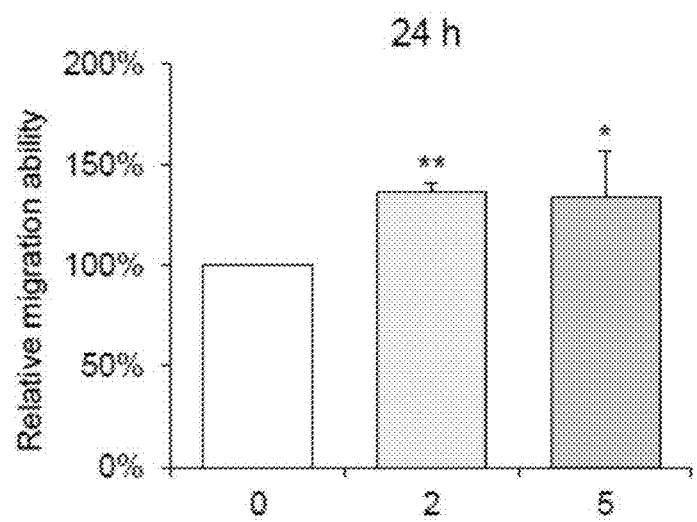
FIG. 2B shows the effects of the peptide of SEQ ID NO: 1 in enhancing the migration of the CCD-966SK cells for 24 hours (upper panel) and 48 hours (lower panel); wherein the results were obtained from two independent experiments ($*P<0.05$; $**P<0.01$).
Figure 2B:
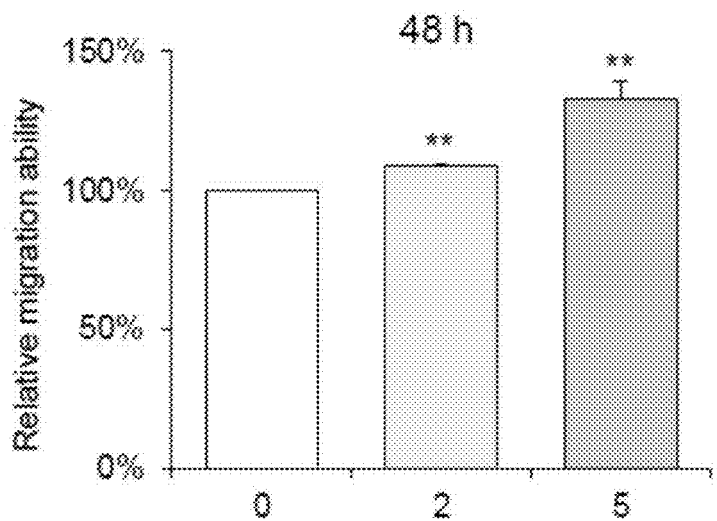

The migration of the CCD-966SK fibroblast cells was analyzed by transwell migration assay. As shown in FIGS. 2A and 2B, it was indicated that the peptide of SEQ ID NO: 1 had the effect in enhancing the migration of the CCD-966SK fibroblast cells.

Example 5: MTT Assay

The cells ($3 \times 10^3$) in 100 μl complete DMEM were seeded in 96-well plates with or without MUC20 peptide NO.10. Ten microliters of 5 mg/ml 3-(4,5-dimethyl-2-thiazolyl)-2, 5-diphenyl-2H-tetrazolium bromide solution (MTT; Sigma) was added to each well and incubated at 37° C. for 3 hours. After that, 100 μl 10% SDS in 0.01N HCl was added to dissolve the MTT formazan crystals. The resultant optical density was measured by spectrophotometry at dual wavelengths, 550 and 630 nm.

Figure 3:
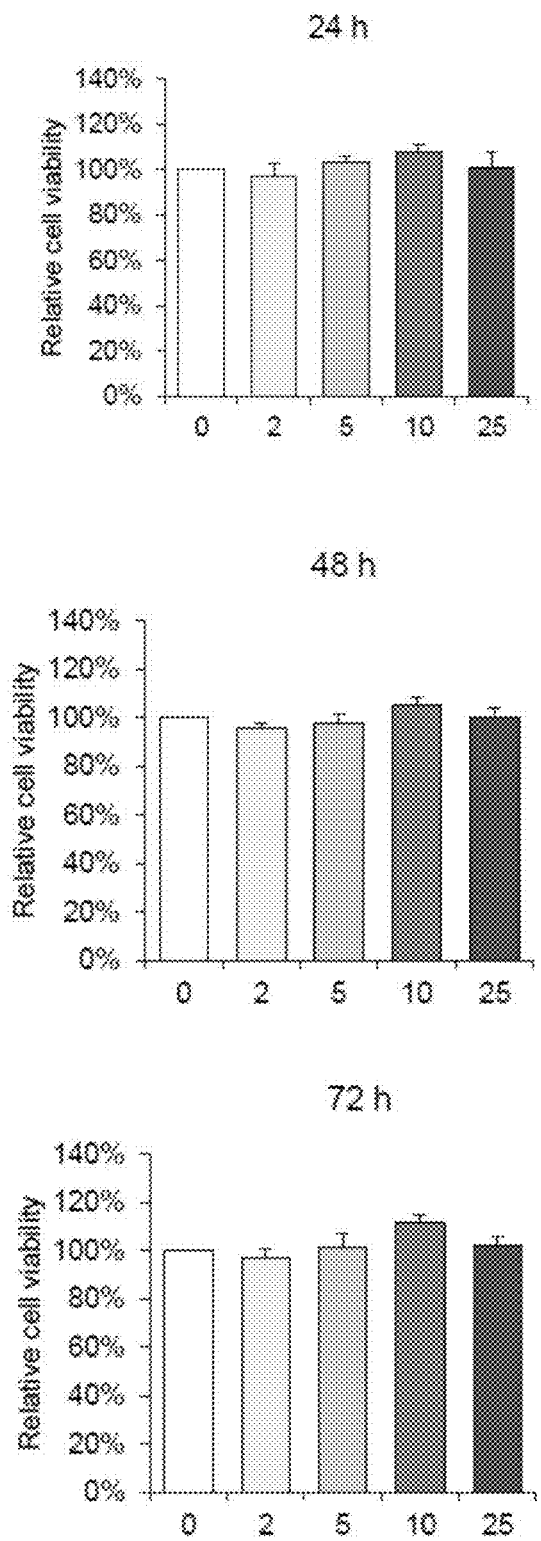
FIG. 3 shows that the peptide of SEQ ID NO: 1 did not significantly affect viability of the CCD-966SK fibroblast cells; wherein the CCD-966SK cells were treated with the peptide of SEQ ID NO: 1 at different concentrations for 24 hours (upper panel), 48 hours (middle panel) and 72 hours (lower panel); wherein the cell viability was analyzed by MTT assays, and the results were obtained from three independent experiments

The cell viability of the CCD-966SK fibroblast cells was analyzed by MTT assays. The results were obtained from three independent experiments. The results of the cells treated with the peptide of SEQ ID NO: 1 for 24 hours (upper panel), 48 hours (middle panel), and 72 hours (lower panel) were shown in FIG. 3. It was found that the peptide of SEQ ID NO: 1 did not significantly affect viability of the CCD-966SK fibroblast cells.

Given the above, it is concluded that the peptide of SEQ ID NO: 1 provide anti-aging effect through the enhancement of the expression of collagen and/or elastin in fibroblast cells and the migration of fibroblast cells, instead of the cell viability of fibroblast cells.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. An anti-aging composition formulated as a topical formulation comprising an effective a mount of a peptide consisting of the amino acid sequence of SEQ ID NO:1; and at least one acceptable carrier, wherein the carrier enhances skin penetration of the peptide.

2. The composition of claim 1, wherein the peptide has an effect in enhancing the expression of collagen or elastin in fibroblast cells, or the migration of fibroblast cells.

3. The composition of claim 1, wherein the peptide is in an amount effective to enhance the expression of collagen or elastin in the fibroblast cells, or to enhance the migration of fibroblast cells.

4. The composition of claim 1, wherein the topical formulation comprises an ointment, lotion, cream, gel, drop, spray, liquid or face mask.

5. The composition of claim 4, wherein the topical formulation is a cream.

6. The composition of claim 4, wherein the topical formulation is a face mask.

7. The composition of claim 1, wherein the carrier further comprises 0.8% saline, 0.3% glycine, or hyaluronic acid.

8. The composition of claim 1, wherein the carrier is dimethylsulfoxide, ethanol, liposome, 2-pyrrolidone, or oleic acid.

9. A personal care method for remedy of damage caused by aging, which comprise topically administering to a subject in need thereof the composition of claim 1 in an amount effective to enhance the expression of collagen or elastin in the fibroblast cells, or to enhance the migration of fibroblast cells in the subject.

10. The method of claim 9, which is for skin care.

11. The method of claim 10, which is used for anti-aging, brightening skin and reducing of wrinkling and fine lines.

* * * * *